US012779365B2

(12) United States Patent
Ditta et al.

(10) Patent No.: US 12,779,365 B2
(45) **Date of Patent: *Nov. 3, 2026**

(54) PROCESS FOR THE SEPARATION OF PINITOL FROM A CAROB EXTRACT

(71) Applicant: BONO & DITTA S.P.A., Campobello di Mazara (IT)

(72) Inventors: Fabio Salvatore Ditta, Campobello di Mazara (IT); Andrea Amato, Marsala (IT)

(73) Assignee: BONO & DITTA S.P.A., Campobello di Mazara (IT)

( * ) Notice: Subject to any disclaimer, the term of this patent is extended or adjusted under 35 U.S.C. 154(b) by 400 days.

This patent is subject to a terminal disclaimer.

(21) Appl. No.: 17/607,143

(22) PCT Filed: Apr. 30, 2020

(86) PCT No.: PCT/IB2020/054084
§ 371 (c)(1),
(2) Date: Oct. 28, 2021

(87) PCT Pub. No.: WO2020/225665
PCT Pub. Date: Nov. 12, 2020

(65) Prior Publication Data

US 2022/0177396 A1 Jun. 9, 2022

(30) Foreign Application Priority Data

May 3, 2019 (IT) ........................ 102019000006530

(51) Int. Cl.
*C07C 29/86* (2006.01)
*C07C 41/36* (2006.01)

(52) U.S. Cl.
CPC .............. *C07C 29/86* (2013.01); *C07C 41/36* (2013.01)

(58) Field of Classification Search
CPC ....... C07C 41/36; C07C 29/86; C07C 43/196; B01D 15/1821; B01D 15/361; B01J 39/26; B01J 41/20
See application file for complete search history.

(56) References Cited

U.S. PATENT DOCUMENTS 5,451,262 A 9/1995 Diaz
5,624,500 A 4/1997 Sanjuan Diaz
(Continued)

FOREIGN PATENT DOCUMENTS

CN 1128986 A 8/1996
CN 101967091 A 2/2011
(Continued)

OTHER PUBLICATIONS

Combined Chinese Office Action and Search Report issued Jun. 23, 2022, in corresponding Chinese Patent Application No. 202080032948.9 (with English Translation), 18 pages.
(Continued)

*Primary Examiner* — Amy C Bonaparte
(74) *Attorney, Agent, or Firm* — Oblon, McClelland, Maier & Neustadt, L.L.P.

(57) ABSTRACT

A process is described for the separation of at least one inositol from a carob extract. The carob extract is filtered and demineralized, and has a Brix value greater than 60 and a pinitol content of 5 to 25 wt %. The carob extract is subjected to chromatographic separation which involves at least one passage on a chromatographic resin. This produces an aqueous solution comprising 35 to 70 wt % pinitol and a Brix value of 20 or lower. The aqueous solution is then purified to obtain a purified aqueous solution having a pinitol content of more than 55%.

20 Claims, 10 Drawing Sheets

(56) References Cited

U.S. PATENT DOCUMENTS

| | | | | |
|---|---|---|---|---|
| 6,699,511 | B2 * | 3/2004 | Macias Camero | C07C 41/36 435/410 |
| 7,361,273 | B2 * | 4/2008 | Heikkila | B01D 15/363 210/659 |
| 2003/0040609 | A1 | 2/2003 | Macias Camero et al. | |
| 2011/0048413 | A1 | 3/2011 | Foraci et al. | |
| 2024/0400483 | A1 * | 12/2024 | Ditta | B01D 15/361 |

FOREIGN PATENT DOCUMENTS

| | | | | |
|---|---|---|---|---|
| CN | 104961628 | A * | 10/2015 | C07C 29/10 |
| EP | 0 617 133 | A2 | 9/1994 | |
| EP | 1 241 155 | A1 | 9/2002 | |
| EP | 2 272 990 | A1 | 1/2011 | |
| ES | 2 234 422 | A1 | 6/2005 | |
| JP | 2001-299400 | A | 10/2001 | |
| JP | 2011-217696 | A | 11/2011 | |
| KR | 10-2004-0016338 | A | 2/2004 | |
| WO | WO 2016/093251 | A1 | 6/2016 | |

OTHER PUBLICATIONS

Combined Chinese Office Action and Search Report issued Feb. 15, 2023 in Patent Application No. 202080032948.9 (with English language translation and English translation of Category of Cited Documents), 10 pages.

International Search Report mailed on Jul. 8, 2020 in PCT/IB2020/054084 filed on Apr. 30, 2020 (3 pages).

* cited by examiner

PROCESS FOR THE SEPARATION OF PINITOL FROM A CAROB EXTRACT

CROSS-REFERENCE TO RELATED APPLICATIONS

The present application is the national stage of international application PCT/IB2020/054084, filed on Apr. 30, 2020, and claims the benefit of the filing date of Italian Appl. No. 10 2019 000006530, filed on May 3, 2019.

FIELD OF APPLICATION

The present invention relates in general to the sector of the food supplement industry, in particular pinitol-based food supplements.

In particular, the invention relates to a process for the separation of pinitol from carob extracts.

PRIOR ART

Pinitol (3-O-methyl-1,2,4 cis-3,5,6 transhexahydroxycyclohexanol or 3-O-methyl-D-chiro-inositol) is a methyl ether of the D-chiro-inositol ($C_7H_{14}O_6$) having molecular mass 194.18 g/mol.

Pinitol (or D-pinitol) is known for its hypoglycemic effect and for its capability of improving the functionality of insulin when administered orally, and for its application in the treatment of diabetes and obesity. Pinitol also improves the absorption of creatine in equal measure to its intake in conjunction with carbohydrates. Said action allows the desired amount of creatine to be taken with no need of having to take large quantities of carbohydrates.

In addition, pinitol enhances the function of muscle tissue, increases the production of glycogen in the muscles and stimulates the transport of glucose within the muscle tissue. Said activities of the pinitol can be exploited in the sports field for improving athletes' performances. In fact, pinitol has the effect of increasing the uptake of glucose into the muscle cell and of increasing glycogen stores stored within the muscles. This leads to more stable blood sugar levels and greater energy levels lasting longer over time.

Pinitol is used by means of oral administration in the form of a supplement or included in food or drink, in a dosage from 0.1 mg to 1.0 g per day per kg of body weight. It can also be administered parenterally or intravenously.

Pinitol was isolated for the first time in pine but it is also present in soy in a concentration of about 1% (in weight percent based on the dry weight of soy). It is estimated that in some Asian countries, where soy consumption is very widespread, the intake of pinitol through soybeans is greater than 5 mg/kg/day.

Pinitol is also present in the plants of *Bougainvillea spectabilis* and *Gliricidia sepium*. Pinitol is also contained in the carob fruit (*Ceratonia siliqua*), from which it can be extracted by chromatographic techniques.

The carob tree is a long-living evergreen and broad-leaved fruit tree with slow growth. In the food sector, carob paste and seeds are used in the production of chocolate substitutes, while many food thickeners and gelling agents are obtained from carob seed flour.

The carob extract usually has the following composition (in weight percent based on the dry weight of the carob extract): sucrose 40-65%; pinitol 7-15%; fructose 7-17%; glucose 7-15%; impurities 0.5-2%. Carob is therefore a very rich source of pinitol, greater for example than soy and pine needles (0.5-1% of pinitol).

Patent EP 1 241 155 B1 (Compania General del Algarrobo de Espana, S.A.) describes a process for the separation of pinitol from carob extracts in which the sucrose contained in the extracts is inverted to fructose and glucose and the syrup thus obtained is subjected to chromatographic separation of the pinitol from the sugars contained in the syrup, in particular by means of a strong cationic resin, thus obtaining a solution of pinitol in water having a purity greater than 90%. Pinitol is then separated from the solution.

Patent application KR20040016338 A (Amicogen Co. Ltd) describes a method for the separation of the pinitol from a carob syrup, which comprises a step of culturing a bacterium, yeast or mold before separation, in order to increase the content of pinitol in the syrup and obtain a product comprising pinitol at a low purity (40-50%). The syrup thus obtained, following the separation of the microorganism cells, is subjected to a treatment by means of activated carbon and to a crystallisation process. The result is a product comprising pinitol at a high purity, even greater than 90%.

Although both of the processes described above allow to obtain pinitol at a purity greater than 90%, they are quite complex and expensive. In fact, in the case of patent EP 1 241 155, various filtration steps are envisaged, followed by a first demineralisation in strong cationic resin (Na), followed by the concentration of the extract, then a step of inversion of sucrose on a cationic resin, followed by a further step of demineralisation by means of passage in anionic resins and finally a chromatography by means of ISMB® for the chromatographic separation of the pinitol. Each of these passages requires the use of large quantities of water, and various steps of concentration of the solutions exiting from each column.

In the case of patent application KR20040016338 the step of culturing the microorganism in the carob syrup requires a subsequent step of separation of the microbial cells. Both of these steps can be difficult on an industrial scale, also due to the fact that they require special measures for the management of microorganisms in the food sector.

Pinitol can also be obtained by chemical synthesis, but this approach is very expensive.

The need is therefore felt in the sector to provide a process for the separation of pinitol (and subsequently of the D-chiro-inositol starting from pinitol) from carob which is simpler and cheaper than the processes of the prior art.

The technical problem underlying the present invention is therefore that of providing a practical, cheap, versatile, scalable and high-yield process for the separation of pinitol (and D-chiro-inositol) from carob, in particular from a carob extract.

SUMMARY OF THE INVENTION

This problem has been solved according to the invention by a process for the separation of at least one inositol from a carob extract comprising the steps of:

a) providing a filtered and demineralised carob extract having a Brix value greater than 60 and a pinitol content, in weight percent based on the weight of the extract, from 5 to 25%;

b) subjecting said carob extract of step a) to a process of chromatographic separation of the pinitol, wherein said process comprises subjecting the extract to at least one passage on a chromatographic resin, thus obtaining an aqueous solution having a pinitol content, in weight percent based on the total weight of the solution, from 35 to 70%, and which has a Brix value of 20 or lower; and c) subjecting the aqueous solution thus obtained in step b) to a purification step, thus obtaining a purified aqueous solution having a pinitol content, in weight percent based on the total weight of the solution, of more than 55%.

The term "pinitol" in the present patent means pinitol in its D configuration (D-pinitol), being D-pinitol the only configuration of the pinitol present in the carob extract.

"Carob extract" means herein the aqueous solution obtained from the maceration and pressing of the previously chopped carob pods, and subsequent separation of the coarse solid residues from the aqueous solution that is obtained.

Preferably, said at least one inositol is selected from pinitol and/or D-chiro-inositol, more preferably pinitol.

Maceration is generally carried out by mixing the pods and water in a weight ratio of about 1 to 3, at a temperature of 60 C-90° C. for 1-24 hours, at a pH comprised between 4.5 and 5.5. Pressing is generally carried out by means of a press, for example in continuous.

The aqueous solution obtained is generally dark in colour and has suspended particles. The aqueous solution thus obtained is furthermore generally composed of glucose, fructose, sucrose, pinitol and other sugars or impurities and normally has a Brix value from 10 to 30.

The filtered extract of step a) can be obtained by filtration techniques known in the sector, preferably by means of a rotary vacuum filter, in which more preferably the filter aid comprises perlite.

Preferably, the perlite has a distribution of particle size greater than 160 μm comprised between 5% (w/w) and 10% (w/w), more preferably 7% (w/w).

Preferably, the perlite has a density value comprised between 90 and 130 g/l, more preferably 110 g/l.

A perlite suitable for the purposes of the present invention is for example Randalite® W24 (Ceca Arkema Group, France).

Perlite is composed of soft rock of aluminium silicate, which expands when heated. This expanded material is ground to create various degrees of filter aid.

Preferably, in addition to or as an alternative to filtration by means of a rotary filter, filtration can comprise a filtration step by means of a bell filter (also known as pre-coat filter), in which filter elements are arranged vertically.

Preferably, the filtering material comprises diatomaceous earth.

Preferably, the diatomaceous earth comprises $SiO_2$.

Preferably, the diatomaceous earth is of the flux-calcined type.

Filtering materials suitable for the purposes of the present invention are, for example, Dicalite Speedplus® or Dicalite 6000 (Palumbo Trading, Srl, Italy).

Preferably, in addition to or as an alternative to filtration by means of a rotary filter and/or filtration by means of a bell filter, filtration can comprise a filtration step by means of passage through the tangential filter, according to techniques known in the sector. Preferably, the tangential filter is equipped with a filter having a pore diameter of 0.45 μm or lower.

Preferably, the carob extract of step a) is concentrated. The concentration is carried out by means of concentration techniques known in the sector, for example concentration with heat, preferably at a temperature from 40 to 90° C., for a flow rate from 6000 to 10000 l/h.

Preferably, the carob extract of step a) is decoloured.

Preferably, the decolouration is carried out by adsorption chromatography.

Preferably, the decolouration is carried out by means of passage of the carob extract on an adsorbent resin, more preferably comprising a styrene-divinylbenzene (DVB) copolymer-based matrix. It is within the skills of the person skilled in the art to select a suitable resin and the process parameters. A suitable resin for decolouration is the adsorbent resin Sepabeads® SP207 of Resindion Srl (Milan, Italy).

Preferably, the carob extract of step a) is demineralised (or rectified) by means of cationic exchange chromatography and anionic exchange chromatography.

Preferably, the carob extract of step a) is demineralised (or rectified) by means of passage of the carob extract on at least one anionic exchange resin and on at least one cationic exchange resin, more preferably a weak anionic exchange resin and a strong cationic exchange resin.

Preferably, the carob extract of step a) is demineralised by means of passage of the carob extract in sequence on at least one anionic exchange resin, more preferably a weak anionic exchange resin, and subsequently on a cationic exchange resin, more preferably a strong cationic exchange resin.

Preferably, the carob extract of step a) is demineralised by means of passage of the carob extract on at least two weak anionic exchange resins and on at least two strong cationic exchange resins.

Preferably, the carob extract of step a) is demineralised by means of passage of the carob extract on two weak anionic exchange resins and on two strong cationic exchange resins.

Preferably, at least one of the passages of the carob extract on a weak anionic exchange resin is followed by the passage of the carob extract on a strong anionic exchange resin, before its passage on a strong cationic exchange resin.

Preferably, said at least one of the passages of the carob extract on a weak anionic exchange resin is the last one.

In a preferred embodiment, demineralisation is carried out subjecting the carob extract in sequence to the following steps:

i. first passage of the carob extract on a weak anionic exchange resin;
ii. first passage of the carob extract on a strong cationic exchange resin;
iii. second passage of the carob extract on a weak anionic exchange resin;
iv. passage of the carob extract on a strong anionic exchange resin; and
v. second passage of the carob extract on a strong cationic exchange resin.

As known, strong ionic exchange resins are operative throughout the pH range from 0 to 12, while the weak ones are able to exchange only in a narrower range. The weak cationic ones operate in an acid range, whereas the weak anionic ones operate in the basic range.

Weak anionic exchange resins suitable in the present invention comprise Relite RAM1® (Resindion S.r.l., Milan, IT), Dowex® MWA-1 (Dow Chemical Company, JP), and Purolite™ A100 (Dow Chemical Company, JP).

Strong anionic exchange resins suitable in the present invention comprise Relite RAP1® (Resindion S.r.l., Milan, IT), Amberlite™ IRA900 (Lenntech BV, NL), and Purolite® A500 (Lenntech BV, NL).

Strong cationic exchange resins suitable in the present invention comprise Relite RPS® (Resindion S.r.l., Milan, IT), Amberlite™ IRC200 (Lenntech BV, NL), and Purolite® A150 (Lenntech BV, NL).

Preferably, the demineralisation step is carried out in continuous, i.e. without interrupting the demineralisation process.

Preferably, the demineralisation step eliminates 100% of the impurities and ions present in the extract.

Preferably, the solution leaving the demineralisation step has a pH comprised between 3 and 5. Within these pH values, in fact, browning of the extract is avoided.

It is within the skills of the person skilled in the art to select a suitable resin and the process parameters.

Preferably, the carob extract of step a) has a Brix value of at least 65.

Brix (° Bx) is a percentage (% w/w) measure of the solid state substances dissolved in a liquid. In the present invention, the measurement of the Brix degrees can be carried out according to one of the methods known in the field, for example by means of a refractometer. A refractometer suitable for the purposes of the present invention is the ATAGO RX-9000CX model (Atago USA, Inc., USA)

Preferably, the extract of step a) has conductivity values from 70 to 110 μS/cm, more preferably from 90 to 100 μS/cm. The conductivity measurement can be carried out according to methods known in the field, for example by means of a conductivity meter.

Preferably, the pH of the carob extract of step a) is from 2 to 4.5, more preferably from 2.5 to 3.5.

Preferably, the carob extract of step a) has an absorbance value from 0.005 to 0.030, more preferably from 0.010 to 0.020, with reading in a quartz cuvette, optical path 1 cm, at 430 nm.

Preferably, the carob extract of step a) comprises, in weight percent based on the weight of the extract, from 5 to 20%, more preferably from 10 to 15%, of pinitol.

Preferably, the carob extract of step a) comprises, in weight percent based on the weight of the extract, from 5 to 15%, more preferably from 8 to 10% of sucrose.

Preferably, the carob extract of step a) comprises, in weight percent based on the weight of the extract, from 5 to 15%, more preferably from 8 to 10% of sucrose; from 5 to 20%, more preferably from 10 to 15% of pinitol; from 20 to 50%, more preferably from 30 to 40% of fructose; from 20 to 50%, more preferably from 30 to 40% of glucose.

Preferably, step b) is carried out by means of passage of the carob extract of step a) on a strong cationic exchange resin (Na+), such as for example the resin Diaion™ UBK530 (Resindion Srl, Milan, Italy). Other resins suitable for the purpose of the present invention are the resins Diaion™ UBK535, UBK550 and UBK555 (Resindion Srl, Milan, Italy).

Preferably, step b) is carried out by means of the (continuous) Simulated Moving Bed Chromatography (SMB Chromatography) technique, more preferably by means of improved (continuous) chromatographic separation ("Improved Simulated Moving Bed" (ISMB)), for example ISMB® (Improved Simulated Moving Bed, Mitsubishi Kasei Corporation).

Preferably, the aforesaid simulated moving bed chromatography technique (SMB Chromatography), preferably the aforesaid continuous chromatographic separation ISMB, in particular ISMB®, is carried out using four columns.

As is known, the simulated moving bed chromatography is a continuous multi-column chromatography process, a technique known since 1961, used in the preparation of purified binary mixtures in a continuous way.

The aforesaid ISMB technique, developed by Mitsubishi Chemical Industries (Tokyo, Japan), represents an improvement over the SMB technique described above and allows the separation of two components.

Preferably, in step b) the elution is carried out with demineralised water.

Preferably, the aqueous solution obtained in step b), has a Brix value of 15 lower, more preferably of 10 or lower.

Preferably, the aforesaid aqueous solution obtained in step b) has, in weight percent based on the total weight of the solution, a pinitol content from 50 to 70%, more preferably from 60 to 70%.

Preferably, the aforesaid aqueous solution thus obtained in step b) has, in weight percent based on the total weight of the solution, a sucrose content from 2 to 8%.

Preferably, the aforesaid aqueous solution thus obtained in step b) has, in weight percent based on the total weight of the solution, a sucrose content from 2 to 8%, a glucose content from 20 to 32%, a pinitol content from 50 to 70%, more preferably from 60 to 70%, a fructose content from 0 to 6%.

Preferably, at the end of step b) a second (waste) solution is also obtained, which has a Brix value from 25 to 40.

Preferably, said second solution has, in weight percent based on the total weight of the solution, a pinitol content of 10% or lower.

Preferably, this second solution has, in weight percent based on the total weight of the solution, a sucrose content from 0 to 4%, a glucose content from 2 to 10%, a pinitol content from 2 to 7%, a fructose content from 85 to 95%.

Preferably, the purification step c) comprises a concentration step, preferably with heat, of the solution obtained in step b).

Preferably, the aforesaid step of concentration with heat of the solution comprises heating the solution to a temperature from 25 to 60° C. until a Brix value of 60 or greater, more preferably of 70 or greater, even more preferably from 70 to 75 is reached.

Preferably, in step c), the concentration of the solution is followed by a crystallisation step of the obtained solution.

Preferably, the crystallisation step is carried out by keeping the concentrated solution at a temperature from 18 to 25° C. for a time from 3 to 10 days, until formation and sedimentation of the crystal.

Preferably, in step c), the crystallisation is completed by adding ethyl alcohol (for example an aqueous solution of 71% vol ethyl alcohol) to the concentrate thus obtained following the sedimentation of the crystal, until formation of a pure crystal.

It is within the capabilities of the skilled person in the field to modulate the parameters and the materials used in the purification step c) in order to obtain the desired result.

Preferably, at the end of the purification step c), a concentrate is obtained comprising pinitol at at least 70%, more preferably at least 80%, even more preferably at least 85%, even more preferably at least 90%, the most preferably at least 95% purity.

In the present patent the purity of a component is to be understood as expressed as a weight percent of the component based on the weight of the solution or of the crystal that contains this component.

Preferably, the concentrate comprising pinitol at greater than 55% purity exiting from step c) is subjected to centrifugation, thus obtaining a sediment comprising pinitol and a supernatant comprising glucose.

Preferably, the thus obtained sediment is subjected to dehumidification under heating, more preferably at about 45° C. for at least two days, thus obtaining pinitol in the form of a white powder, having a purity of at least 95%.

Preferably, step c) is followed by a step d) of subjecting the aqueous solution obtained in step c), or the pinitol obtained following dehumidification of the sediment comprising pinitol, to acid hydrolysis of the pinitol, thus obtaining a solution containing D-chiro-inositol and the subsequent chromatographic separation of the D-chiro-inositol from the solution comprising D-chiro-inositol by means of at least one passage of the aqueous solution comprising D-chiro-inositol on a strong anionic exchange resin, thus obtaining an aqueous solution comprising D-chiro-inositol, preferably, in weight percent based on the total weight of the solution, at least at 95% and preferably having a Brix value of 1 or lower.

Preferably, in step d) the acid hydrolysis is carried out by adding HCl (for example at 33% (v/v)) to an aqueous solution of pinitol.

Preferably, the addition of HCl is followed by a boiling step of the aqueous solution thus obtained for a time of at least 12 hours, more preferably of at least 24 hours.

Preferably, in step d), the strong anionic exchange resin is selected from RAP1® (Resindion S.r.l., Milan, IT), Amberlite™ IRA900 (Lenntech BV, NL), and Purolite® A500 (Lenntech BV, NL), preferably RAP1®.

Preferably, in step d), the passage of the aqueous solution on a strong anionic exchange resin is preceded by a step of decolouration of the aqueous solution, more preferably by adding activated carbon in solution.

Preferably, the activated carbon is added to the solution in a concentration from 50 to 150 g per hectolitre of solution, more preferably from 80 to 120 g per hectolitre of solution.

The activated carbon is preferably selected from activated carbon having a median diameter from 4 to 50 μm, more preferably from 8 to 15 μm.

Preferably, the activated carbon has a BET comprised between 1200 and 2000 $m^2/g$, more preferably comprised between 1500 and 1800 $m^2/g$.

Activated carbon suitable for the purposes of the present invention is for example Picapure HP 120 (Pica Italia SpA, Italy) or Decoran® (AEB®, Italy).

The median diameter (MT50 or d50) is to be understood as measured by means of a laser granulometer and is the diameter which corresponds to 50% by weight of the particles having a smaller diameter and 50% by weight of the particles having a higher weight. Diameter means the size of the particle measured with the laser granulometer as previously described.

The BET surface is intended as measured by means of the ASTM D-3037/89 protocol.

Preferably, in step d), the aqueous solution entering a strong anionic exchange resin has a Brix value of 6.5 or greater.

Preferably, in step d), the aqueous solution leaving a strong anionic exchange resin has a basic pH value, more preferably from 8 to 12.

Preferably, the aqueous solution comprising D-chiro-inositol obtained in step d), leaving the strong anionic exchange resin, is subjected to acidification, thus obtaining an acidified aqueous solution having a pH between 3 and 5, more preferably about 4.

Preferably, the acidification step is carried out with a weak acid, for example citric acid.

Preferably, the aqueous solution comprising D-chiro-inositol obtained in step d) is subjected to concentration, thus obtaining a concentrated aqueous solution having a Brix value of 60 or greater, more preferably of 65 or greater, even more preferably of 70 or greater.

Preferably, the aqueous concentrated solution thus obtained is subjected to crystallisation, more preferably keeping the aqueous solution at a temperature of about 7-10° C. for 2-6 hours.

Preferably, following crystallisation, D-chiro-inositol is subjected to dehumidification, more preferably to absorption, thus obtaining D-chiro-inositol purified at least at 90%, more preferably at least at 95%.

Preferably, the yield of pinitol, in weight percent with respect to the weight of the carob pods from which pinitol is extracted, is at least 3%, more preferably at least 5%, even more preferably at least 7%, the most preferably from 7 to 10%.

Preferably, the yield of pinitol, in weight percent with respect to the weight of the carob pods from which pinitol is extracted, is of 15% or lower.

Preferably, the yield of pinitol, in weight percent with respect to the weight of the starting pinitol (present in the pods), is of 80% or greater.

Preferably, the process of the present invention is carried out in continuous.

The process of the present invention therefore refers to the separation of pinitol, of D-chiro-inositol, or both. It is in fact possible to carry out the process up to step c) thus obtaining pinitol, or to continue the process thus obtaining D-chiro-inositol starting from pinitol. It is also possible to use only a part of the pinitol for obtaining D-chiro-inositol, thus obtaining both pinitol and D-chiro-inositol.

It has surprisingly been found that, thanks to the process of the present invention, it is possible to make pinitol and/or D-chiro-inositol available at a high degree of purity, in a simpler, faster and cheaper way than the processes of the prior art.

In fact, the process of the present invention envisages a relatively small number of passages with respect to the prior art.

Furthermore, thanks to the presence of a demineralisation step, particularly when carried out according to the preferred embodiments of the present invention, it is possible to carry out the separation of the pinitol starting from a relatively highly concentrated aqueous solution having a relatively high concentration of pinitol. This expedient allows to make the process more streamlined, since relatively low volumes of aqueous solution are involved (the pinitol content being equal). In addition, a relatively lower amount of water will be required for dilution, at each chromatography passage, with consequent lower costs and waste.

In a preferred embodiment, in the demineralisation step, the adopted sequence of the resins, in particular the preferred sequence i-v, which comprises in sequence i) a weak anionic resin, ii) a strong cationic resin, iii) a weak anionic resin, iv) a strong anionic resin, and finally v) a strong cationic resin, is particularly advantageous.

The alternation of an anionic and cationic resin, as well as the alternation of a strong and weak ionic exchange resin, allows to have a particularly high recovery of the pinitol. It is also particularly advantageous if the last passage is carried out on a strong cationic resin because this causes the exiting solution to have an acid pH, thus avoiding the browning of the solution and therefore the need to carry out a dedicated decolouration step.

A further advantage of the method of the present invention is that it can be carried out in continuous. This entails greater simplicity, automation and process speed compared to discontinuous processes.

DETAILED DESCRIPTION OF THE INVENTION

Figure 1:
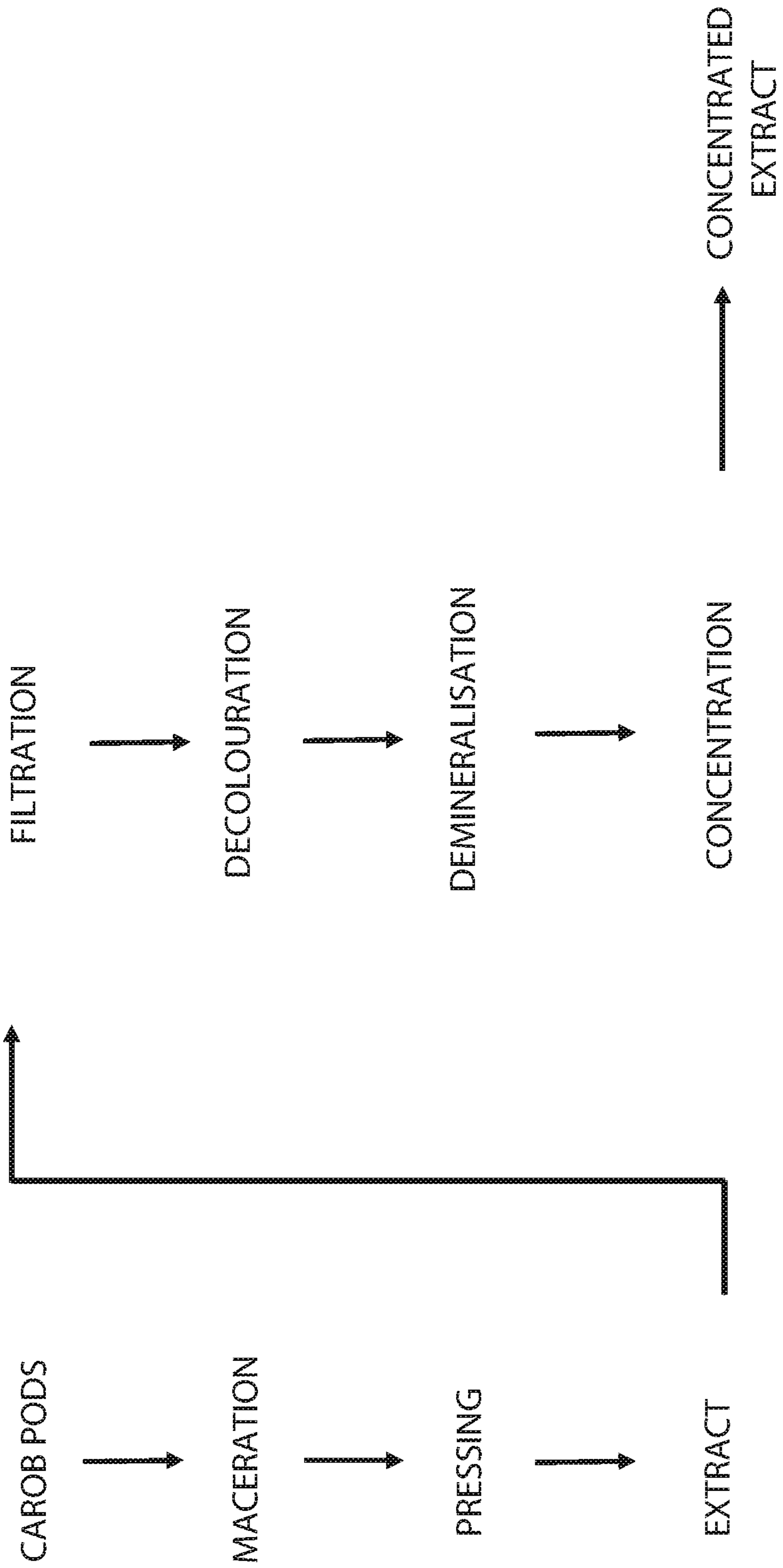
FIG. 1 is a block diagram of a preferred embodiment of part of the process of the present invention, starting from carob pods until an aqueous solution is obtained with a pinitol content, in weight percent based on the total weight of the solution, from 35 to 70%, and having a Brix value of 20 or lower, of step b).
Figure 2:
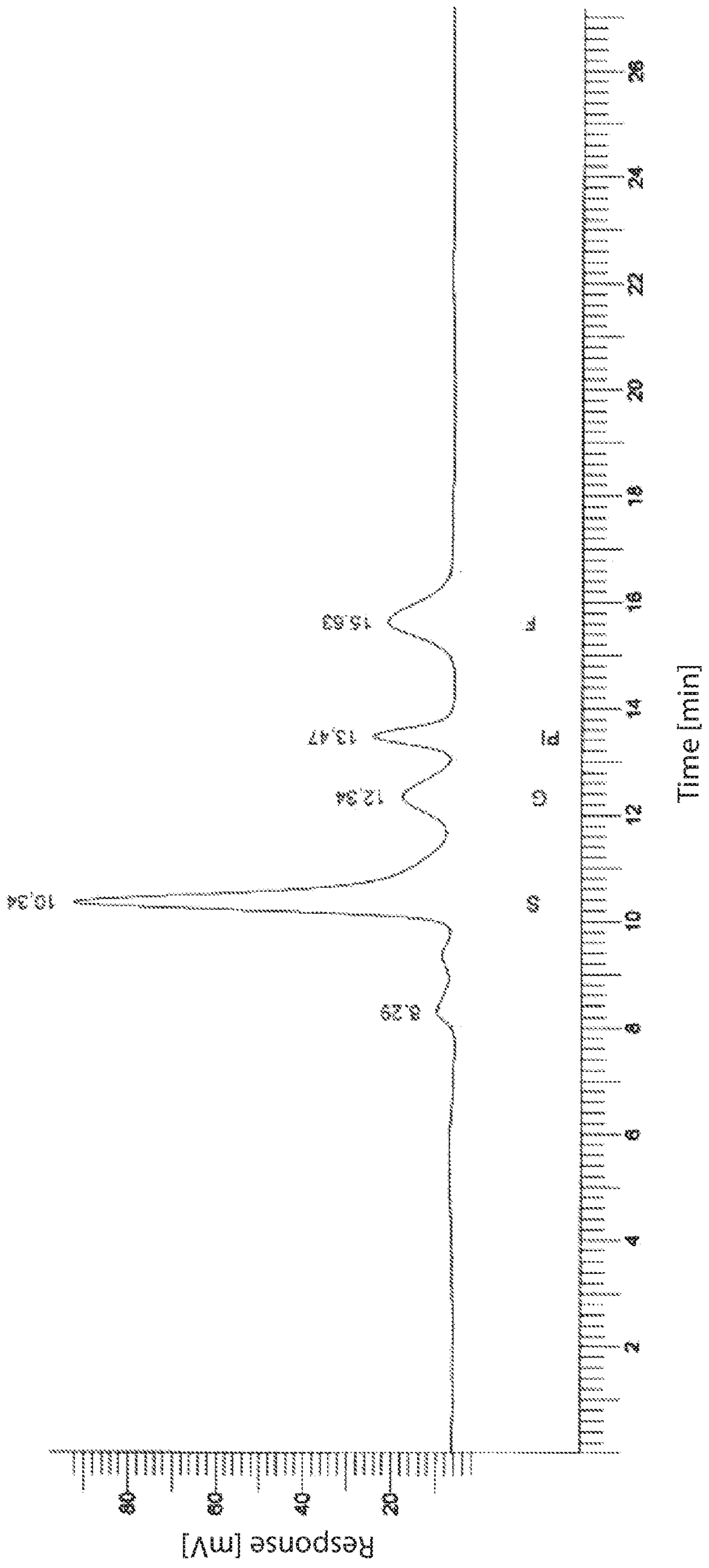
FIG. 2 shows the results of the HPLC analyses relating to the determination of the composition of the macerated and pressed carob extract described in Example 1.
Figure 3:
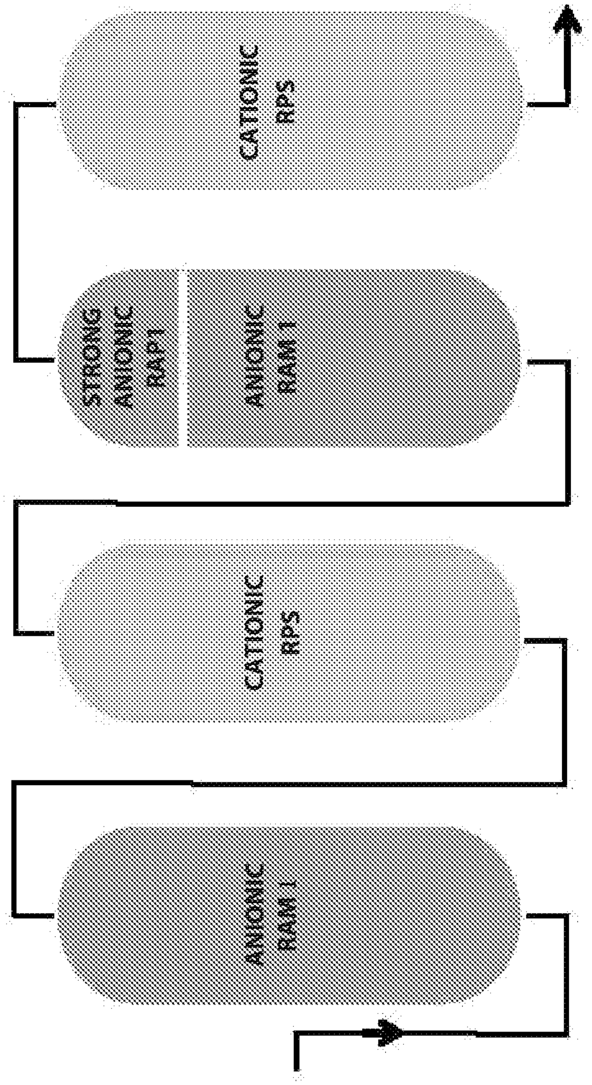
FIG. 3 is a diagram of the passages relating to the demineralisation step according to a preferred embodiment of the invention (Example 1).
Figure 4:
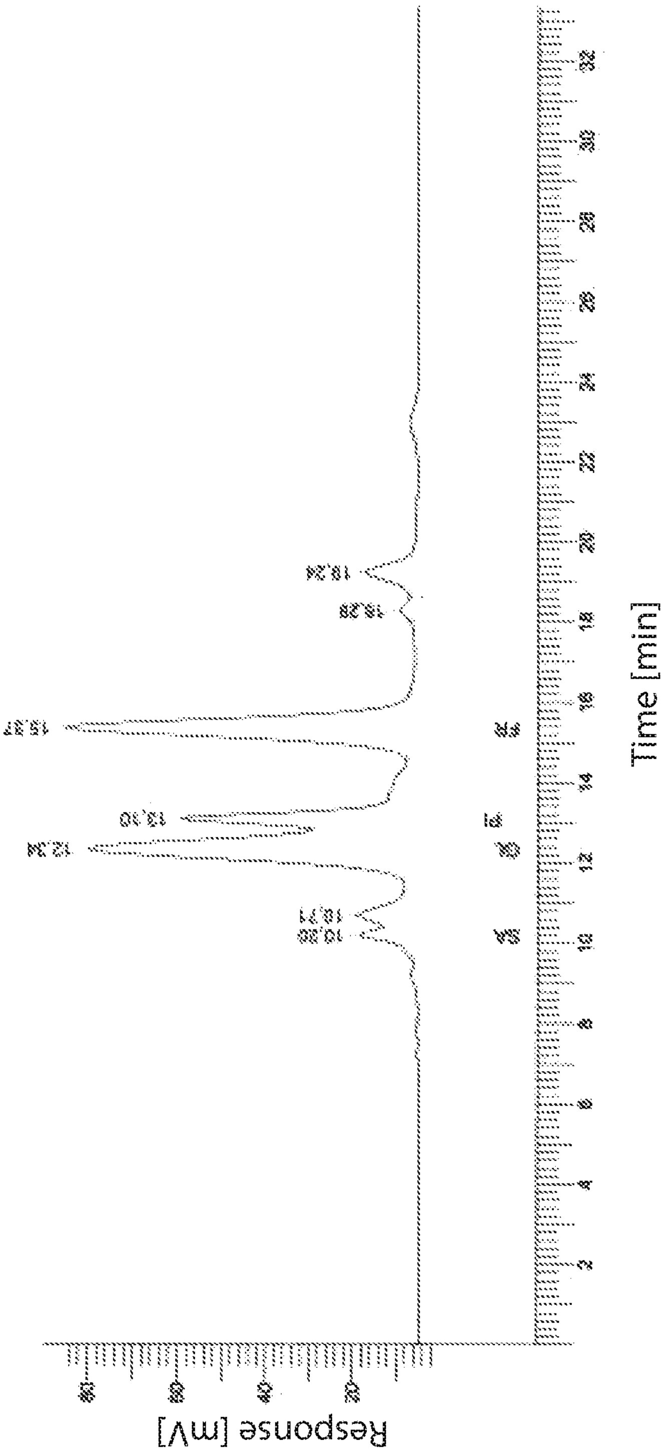
FIG. 4 shows the results of the HPLC analyses relating to the determination of the composition of the filtered, decoloured, rectified (demineralised) and concentrated carob extract described in Example 1.
Figure 5:
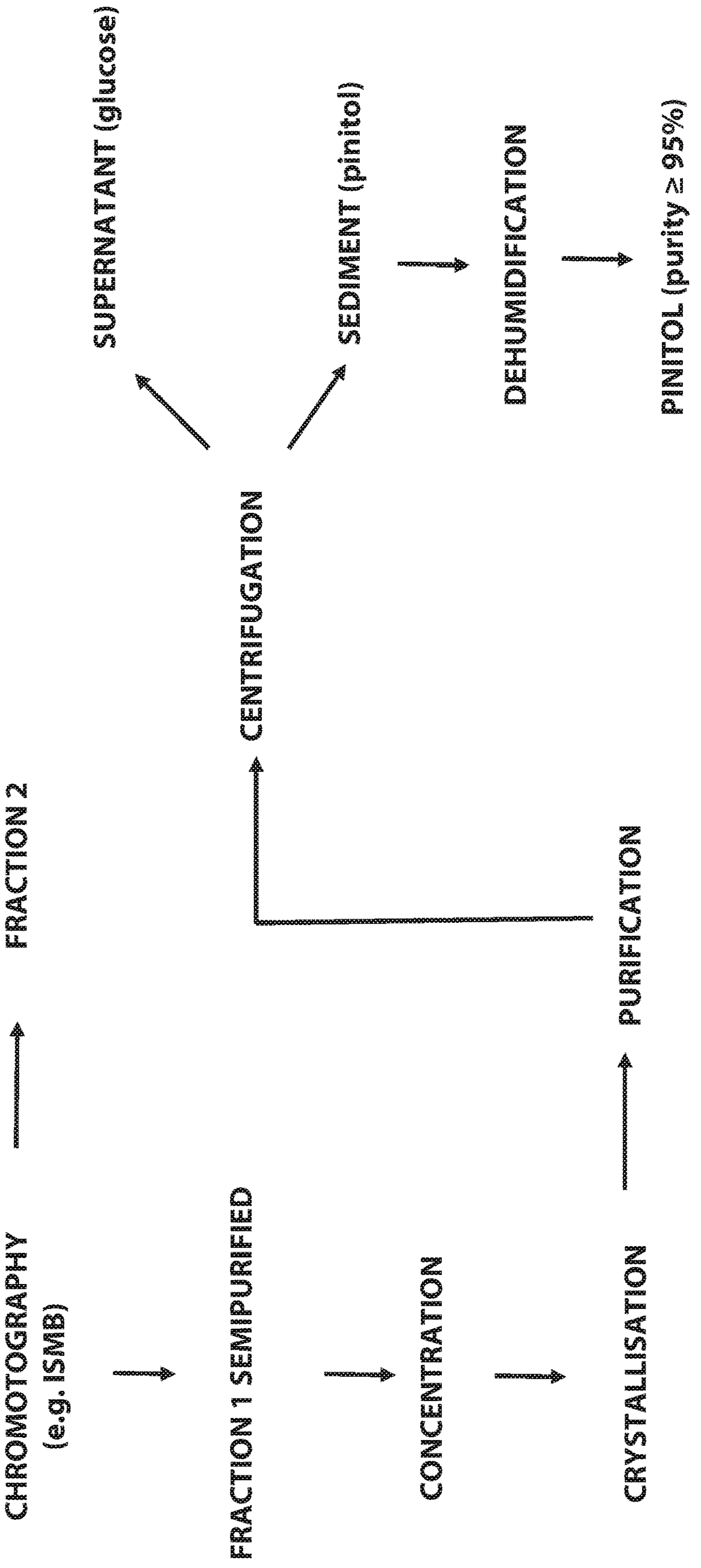
FIG. 5 is a block diagram of a preferred embodiment of part of the process of the present invention, starting from the aqueous solution with a pinitol content, in weight percent based on the total weight of the solution, from 35 to 70%, and having a Brix value of 20 or lower, of step b) until the purified aqueous solution, of step c), is obtained (Example 1).

The invention will now be further described with reference to embodiment examples provided for illustrative and non-limiting purposes.

Example 1

Process for the Separation of Pinitol (FIGS. 1-8)

500 kg of carob pods were chopped until fragments of pods of about 1 cm in size were obtained and these fragments were macerated by mixing one part of the pods and three parts of water at 75° C. The fragments were then pressed, thus obtaining a carob extract having the following composition (in percent by dry weight on the dry weight of the juice): sucrose 62.5%; glucose 11.2%; pinitol 10.1%; fructose 16.1%; impurities 0.5% (composition in FIG. 2).

The aforesaid composition was determined by means of HPLC, eluent $H_2O$, flow 0.6 ml/min, column temperature 75° C., column size 8 mmI.D, 300 mm column, functional group Ca, cationic exchange resin.

The obtained extract also had a Brix value of 18.

The extract was filtered with a rotary filter under vacuum using Perlite Randalite® W24 (Ceca Arkema Group, France) as a filter aid.

The filtrate was then subjected to a second filtration, with a bell filter, with filter elements arranged vertically, and having diatomaceous earth, in particular Dicalite Speedplus (Palumbo Trading Srl. Italy) as aid material.

The filtrate was then subjected to a third filtration, with the passage through the tangential filter, using membranes having a pore size of about 0.45 μm as filter elements.

The extract thus filtered was then passed on a Sepabeads SP207® (Resindion S.r.l., Italy) adsorbent resin for decolouration; and then subjected to demineralisation (or rectification) by means of passage on the following resins, in the described order (see diagram in FIG. 3):

1) Column 1: Relite RAM1/M (Resindion S.r.l., Milan, IT) (weak anionic);
2) Column 2: Relite RPS (Resindion S.r.l., Milan, IT) (strong cationic);
3) Column 3: Relite RAM1/M (Resindion S.r.l., Milan, IT) (weak anionic);
4) Column 3: Relite RAP1 (Resindion S.r.l., Milan, IT) (strong anionic); and
5) Column 4: Relite RPS (Resindion S.r.l., Milan, IT) (strong cationic).

Table 1 shows the characteristics of each single resin.

TABLE 1

| | RESIN 1 Anionic RAM 1 | RESIN 2 Cationic RPS | RESIN 3 Anionic RAM 1 | RESIN 4 Strong Anionic RAP 1 | RESIN 5 Cationic RPS |
|---|---|---|---|---|---|
| Capacity Liters | 12000 | 14000 | 12000 | 4000 | 5000 |

Table 2 shows the operating conditions of each single column.

TABLE 2

| | RESIN 1 Anionic RAM 1 | RESIN 2 Cationic RPS | RESIN 3 Anionic RAM 1 | RESIN 4 Strong Anionic RAP 1 | RESIN 5 Cationic RPS |
|---|---|---|---|---|---|
| pH | 11-6 | 1-8 | 11-6 | 11-6 | 2-6 |
| Conductivity μS/cm | <4000 | <4000 | <500 | <500 | <150 |
| Total quantity of processed product | | | 100 $m^3$ | | |

Table 3 shows the characteristics of the four resins mentioned above.

TABLE 3

| | Sepabeads SP207 (adsorbent resin) | Relite RAP1 (strong anionic) | Relite RPS (strong cationic) | Relite RAM1 (weak anionic) |
|---|---|---|---|---|
| Matrix | Styrene-DVB copolymer | Styrol-DVB porous copolymer | Highly porous styrol-DVB copolymer | Highly porous styrene-DVB copolymer |
| Functional group | | Trimethyl-amine | Sulphonic | Tertiary amine |
| Colour and physical | Yellowish brown | Light yellow opaque | Light brown opaque spheres | Light yellow opaque |

TABLE 3-continued

| | Sepabeads SP207 (adsorbent resin) | Relite RAP1 (strong anionic) | Relite RPS (strong cationic) | Relite RAM1 (weak anionic) |
|---|---|---|---|---|
| form | | spheres | | spherical beads |
| Particle size distribution | | 0.425-1.18 mm | 0.425-1.18 mm | 0.425-1.18 mm |
| Ionic form supplied | | $Cl^-$ | $N6^+$ | Free base |
| Total exchange capacity | 1.18 min eq/l | 1.2 min eq/l | 1.18 min eq/l | 1.5 min eq/l |
| Chemical stability | Stability within pH | Stability within pH | Stability within pH | Stable over the entire pH range |
| Thermal stability | 130° C. | 60° C. max (OH); 80° C. max (Cl) | 120° C. max | 100° C. max |

Table 4 shows the operating conditions of the four resins mentioned above.

TABLE 4

| | Sepabeads SP207 (adsorbent resin) | Relite RAP1 (strong anionic) | Relite RPS (strong cationic) | Relite RAM1 (weak anionic) |
|---|---|---|---|---|
| pH range | 0-14 | 0-12 | 0-14 | 0-9 |
| Operative linear flow rate | | 5-50 m/h | 5-50 m/h | 5-50 m/h |
| Regenerant | NaOH/Ethyl Alcohol | NaOH | HCl | NaOH |
| Regenerant level | | 50-150 g/l | 40-150 g/l | 60-80 g/l |
| Displacement volume | 1.5-2 BV | 1.5-2 BV | 1.5-2 BV | 1.5-2 BV |
| Washing volume | 4-10 BV | 4-10 BV | 3-5 BV | 4-8 BV |

The extract therefore had conductivity values of 100 µS/cm, pH 3.10, and with regards to the colour a reading of 0.015 (reading Abs 430, optical path of the quartz cuvette 1 cm).

The extract thus obtained was then concentrated with heat, under vacuum conditions, passing from a temperature of 80° C. at the inlet to a temperature of 45° C. at the outlet, reaching 65° Bx. The extract had the following composition (in percent by dry weight on the dry weight of the juice): sucrose 5%; glucose 38%; pinitol 15%; fructose 38%; impurities 4% (see FIG. 4).

The aforesaid composition was determined, as described above, by means of HPLC, eluent $H_2O$, flow 0.6 ml/min, column temperature 75° C., column size 8 mmI.D, 300 mm column, functional group Ca, cationic exchange resin. The concentrated extract thus obtained was then fed to an ISMB® plant (Improved Simulated Moving Bed, Mitsubishi Kasei Corporation) consisting of 4 UBK 530 columns (Resindion srl, Milan, Italy) and using demineralised water for elution.

Other operation parameters are summarised in Table 5.

TABLE 5

| | |
|---|---|
| Resin volume | 124 l |
| Flow rate | 59-60.6 l/h |
| W/F | 2.7 |
| P/R | 2.4 |
| Temperature | 60° C. |
| Feed capacity | 44-45 l/h |
| Capacity of the pinitol fraction | 16-17.8 l/h |

Key:
W: water flow rate
F: feed rate
P: purified solution volume
R: concentrate volume ("waste")

Table 6 shows the ISBM operating conditions

TABLE 6

| FLOW RATE SET | |
|---|---|
| Feed flow rate (Sop) (l/h) | 16.39 |
| Water flow rate (Wop) (l/h) | 44.25 |
| Purified solution flow rate (Fop) (l/h) | 42.8 |
| Concentrate flow rate (Gop) (l/h) | 17.83 |
| Recycle flow rate (R0op) (l/h) | 44.25 |
| **VOLUME SET** | |
| Feed volume (Qsop) (l) | 2.6 |
| Water volume (Qwop) (l) | 7.13 |
| Purified solution volume (Qfop) (l) | 6.89 |
| Concentrate volume (Qgop) (l) | 2.87 |
| Recycle volume (Q0op) (l) | 16.43 |
| **DURATION OF THE STEPS** | |
| (T1op) FEED TIME (sec) | 580.04 |
| (T0op) RECYCLING TIME (sec) | 1336.62 |

Figure 6:
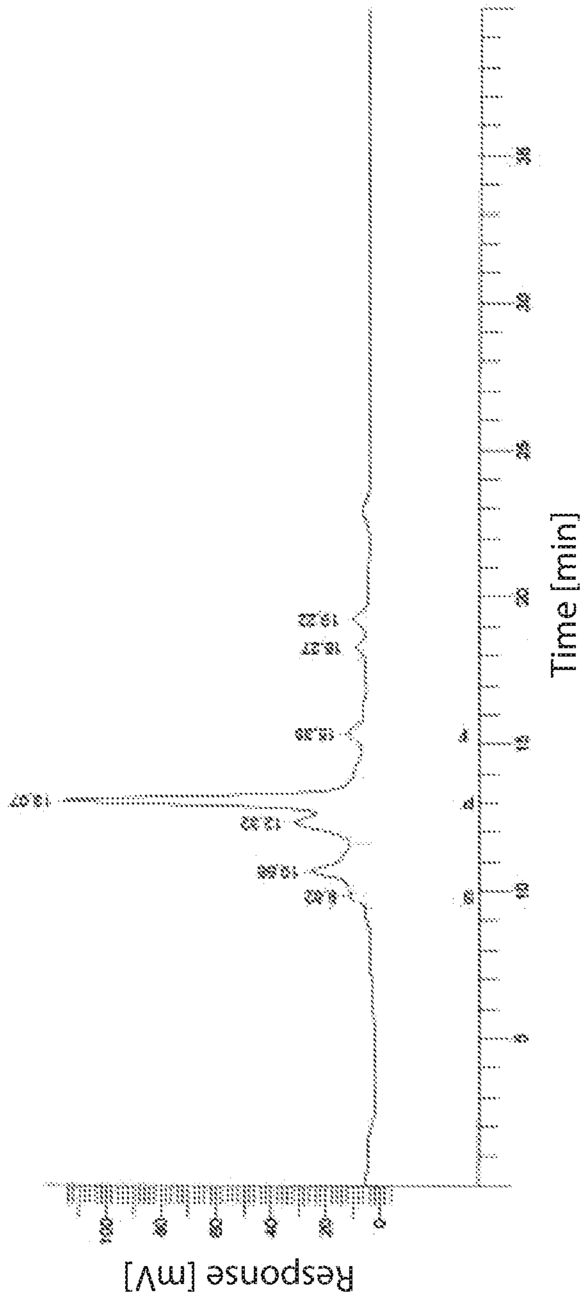
FIG. 6 shows the results of the HPLC analyses relating to the determination of the composition of the aqueous solution with a pinitol content, in weight percent based on the total weight of the solution, from to 70%, and having a Brix value of 20 or lower obtained in step b) described as a fraction 1 in Example 1.
Figure 7:
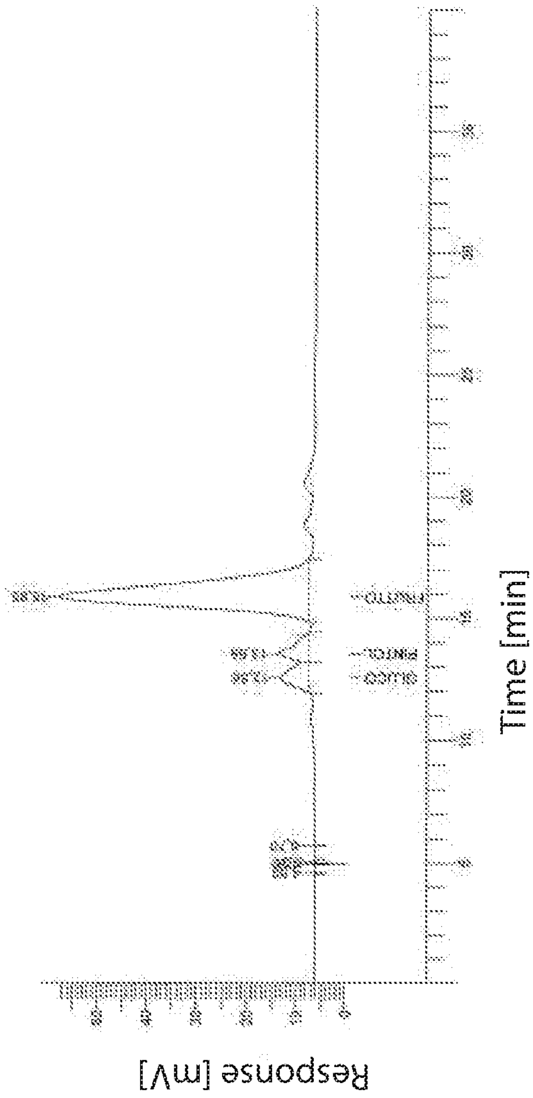
FIG. 7 shows the results of the HPLC analyses relating to the determination of fraction 2 described in Example 1.
Figure 8:
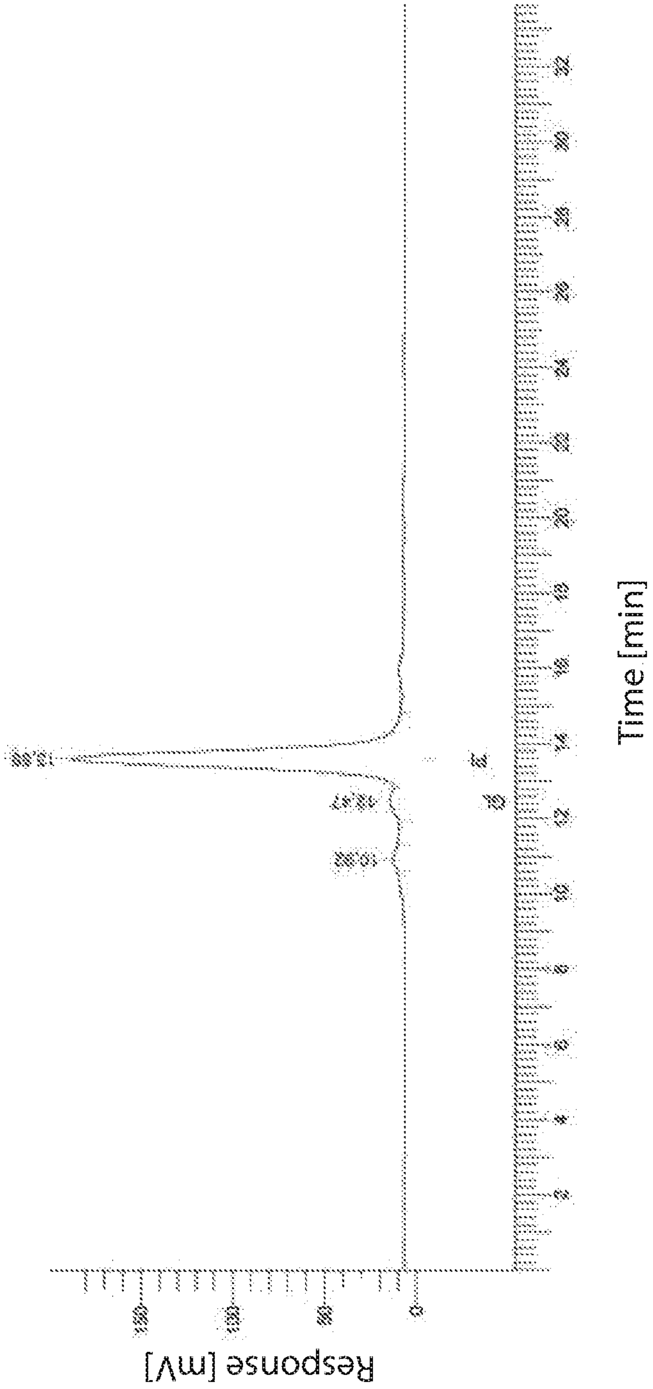
FIG. 8 shows the results of the HPLC analyses relating to the determination of the composition of the purified aqueous solution with a pinitol content, in weight percent based on the total weight of the solution, greater than 55% obtained in step c) described in Example 1.

From this chromatography two liquid fractions were obtained, having compositions summarised in Table 7 (see FIGS. 6 and 7, respectively).

TABLE 7

| | Fraction 1 (purified) | Fraction 2 (waste) |
|---|---|---|
| Brix | 10 | 27 |
| Sucrose | 2.5 | 0 |
| Glucose | 21 | 7.3 |
| Pinitol | 70 | 6.3 |
| Fructose | 3 | 86 |

The aforesaid composition was determined by means of HPLC, as described above.

Fraction 1, containing 70% of pinitol, was then concentrated with heat under vacuum conditions, passing from a temperature of 80° C. at the inlet to a temperature of 45° C. at the outlet, until Brix values of 73 were obtained, and kept at 20° C. for 5 days, thus obtaining the formation of the crystals of pinitol.

After the formation and sedimentation of the crystal, 71% vol. ethyl alcohol was added to the concentrate in the proportion of two parts of alcohol and five parts of concentrate, to purify the crystal and obtain pinitol with a purity greater than 95%. The composition of the crystal obtained is as follows (in weight percent based on the weight of the concentrate): glucose 3%; pinitol 96.5%; sucrose 0%; fructose 0% (see FIG. 8).

The aforesaid composition was determined by means of HPLC under the conditions described above.

The purified solution was then subjected to centrifugation at 4000 rpm with the formation of a sediment containing pinitol and alcohol and a supernatant containing glucose and alcohol.

The sediment was subjected to dehumidification under heating, keeping it for two days at 45° C. thus obtaining 30 g of a white powder with a purity of the pinitol greater than 95%.

This result corresponds to a yield of 90% of pinitol by weight with respect to the weight of the pinitol present in the starting pods.

A comparison was then made between the white powder sample obtained and a standard pinitol sample, which confirmed the identity of the substance as pinitol.

For this purpose an aliquot of each sample was solubilised in a mixture of MeOH/$H_2O$ in an 80/20 ratio, in order to obtain a concentration of 15 ppm (μg/ml) for each sample.

The samples were analysed in LC/MS (liquid chromatography/mass spectrometry) using a Luna $NH_2$ column (150× 2.2, 3 μm). The analyses were conducted in isocratic elution using the mobile phase consisting of acetonitrile (80%) and water (20%). The analysis method lasts 15 minutes. The flow used is 300 μl/min.

Used instrumentation: Water Micromass Q-TOF Premier Mass Spectrometer.

The analysis confirmed the match between the two samples.

Example 2

Figure 9:
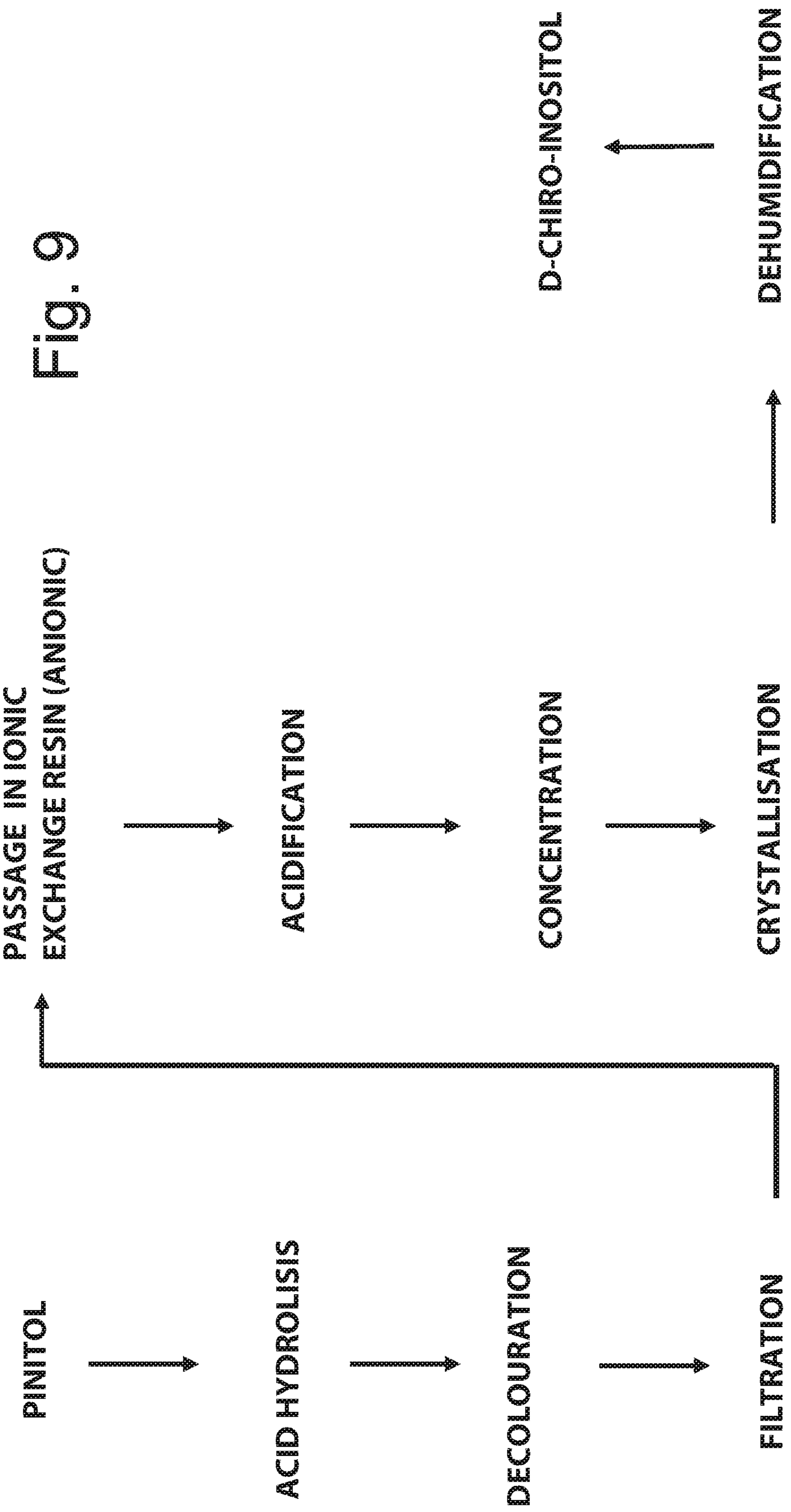
FIG. 9 is a block diagram of a preferred embodiment of part of the process of the present invention, starting from the purified aqueous solution of step c), until the aqueous solution comprising D-chiro-inositol and having a Brix value of 1 or lower, of step d), is obtained. (Example 2).
Figure 10:
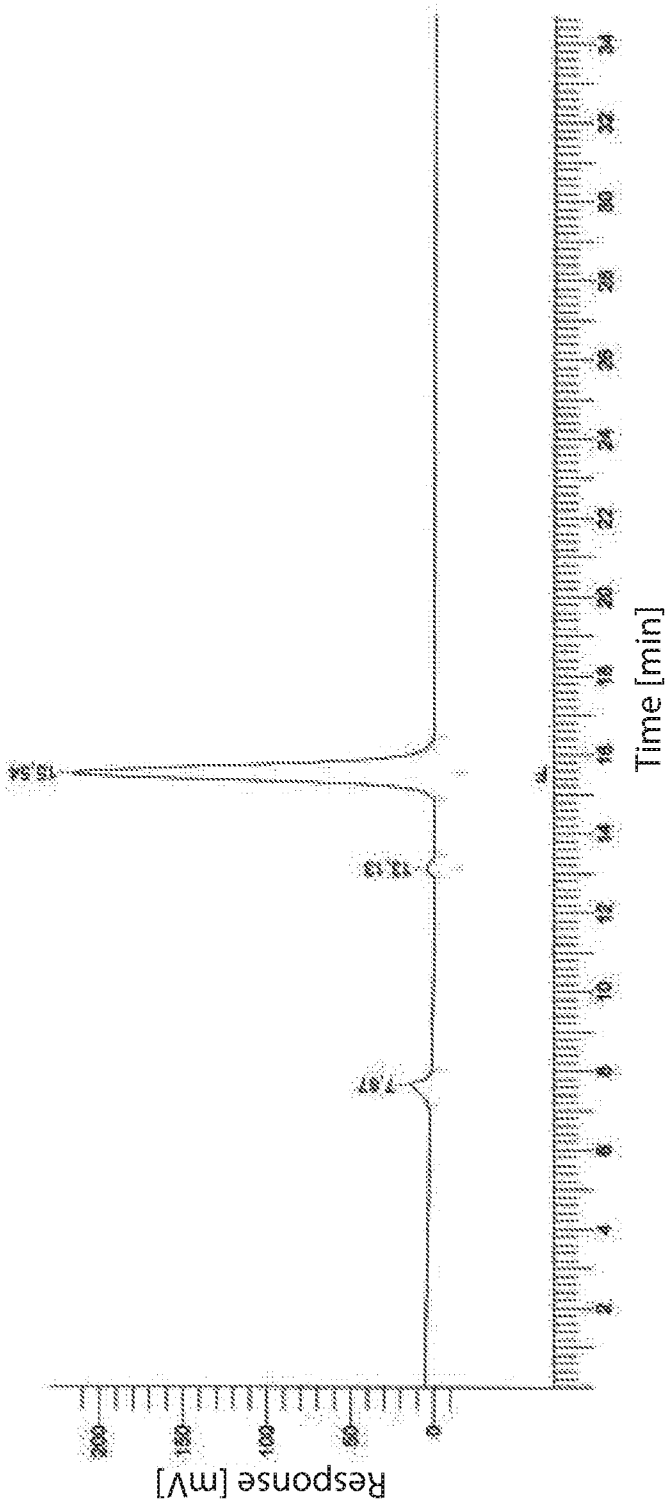
FIG. 10 shows the results of the HPLC analyses relating to the determination of the composition of the aqueous solution comprising D-chiro-inositol and having a Brix value of 1 or lower, of step d), in Example 2.

Process for the Separation of the D-Chiro-Inositol (FIGS. 9, 10)

30 g of powdered pinitol having a purity greater than 95% obtained in Example 1 were added to a 1-litre flask and introduced into 16 g of water and 104 g of 33% HCl were added to this solution.

The solution was heated for 20 minutes (from 45° C. to 60° C.) and 40 ml of 7.2 N HCl were added. At constant reflux, 50 ml of water were added. The solution was then brought to a boil and kept under boiling for 24 hours, during which the reflux remained constant.

After 24 hours, the solution was then subjected to decolouration by adding activated carbon to the solution (from 100 to 150 g/h) while keeping the solution under stirring for 60 minutes, thus obtaining 1160 ml of a solution having a Brix value of 6.5.

The solution was then subjected to filtration to eliminate the brown components formed during heating. The filtration with a rotary filter was carried out under vacuum using a mix at 50% by weight of Dicalite Speedplus® (Palumbo Trading, Srl, Italy) diatomaceous earth and at 50% by weight of perlite Randalite® W24 (Ceca Arkema Group, France) as an aid element.

The solution at this stage had a pH of 1, a clarity in NTU values (Nephelometric Turbidity Units) of 2, and was colourless.

The solution was then neutralised.

The solution was then subjected to passage on a strong anionic exchange resin (Relite RAP1) thus reaching a pH of 9-10 and then the solution was subjected to acidification with citric acid until a pH of 4.0 was reached.

The solution thus obtained had a Brix value of 0.3 and was then concentrated until a Brix value of 70 was reached.

The crystallisation of the D-chiro-inositol was then carried out keeping the solution at a temperature of 8° C. for 24 hours.

The concentrated solution had a D-chiro-inositol content of 95% or greater.

Finally, the concentrated solution was subjected to dehumidification with absorption thus obtaining 29 g of a white powder of D-chiro-inositol with a purity greater than 95%.

This result corresponds to almost 100% yield.

A comparison was then made between the white powder sample obtained and a standard D-chiro-inositol sample, which confirmed the identity of the substance as D-chiro-inositol, using the method described above in Example 1.

The analysis confirmed the match between the two samples.

The invention claimed is:

1. A process for the separation of at least one inositol from a carob extract, comprising, in directly following order:

(1) demineralizing a carob extract by sequentially (a) passing, through a weak anionic exchange resin, the carob extract to obtain a first carob solution; (b) passing, through a strong cationic exchange resin, the first carob solution, to obtain a second carob solution; (c) passing, through a weak anionic exchange resin, the second carob solution, to obtain a third carob solution; (d) passing, through a strong anionic exchange resin, the third carob solution to obtain a fourth carob solution; and (e) passing, through a strong cationic exchange resin, the fourth carob solution, to obtain a demineralized carob extract, extract having a Brix value of greater than 60 and comprising (i) pinitol in a range of from 5 to 25 wt. %, and (ii) sucrose in a range of from 5 to 15 wt. %, based on a total carob extract weight; and without further demineralizing in the process, (2) chromatographically separating pinitol from the demineralized carob extract by at least one passage on a chromatographic resin, to obtain an aqueous solution having a pinitol content, based on a total aqueous solution weight, in a range of from 35 to 70 wt. %, and which has a Brix value of 20 or lower; and (3) purifying the aqueous solution to obtain a purified aqueous solution having a pinitol content, based on total aqueous solution weight, of more than 55 wt. %.

2. The process of claim 1, further comprising, prior to the chromatographically separating (2):

decolorizing the carob extract.

3. The process of claim 1, wherein the demineralized carob extract at a beginning of the chromatographically separating (2) comprises the pinitol in a range of from 5 to 20 wt. %, based on the total demineralized carob extract weight.

4. The process of claim 1, wherein the chromatographically separating (2) comprises simulated moving bed chromatography technique.

5. The process of claim 1, wherein the purifying (3) comprises concentrating the aqueous solution.

6. The process of claim 1, wherein the purified solution comprises the pinitol in at least 70% purity.

7. The process of claim 1, further comprising:

subjecting the aqueous solution to acid hydrolysis of the pinitol to obtain a solution comprising D-chiro-inositol, and subjecting the solution comprising D-chiro-inositol to chromatographic separation of the D-chiro-inositol by at least one passage on a strong anionic exchange resin to obtain an aqueous solution comprising D-chiro-inositol.

8. The process of claim 1, wherein the demineralized carob extract at a beginning of the chromatographically separating (2) comprises the pinitol in a range of from 5 to 10 wt. %, based on the total demineralized carob extract weight.

9. The process of claim 1, wherein the chromatographically separating (2) comprises continuous chromatographic separating.

10. The process of claim 1, wherein the purifying (3) comprises heating and concentrating the aqueous solution.

11. The process of claim 1, wherein the purified solution comprises the pinitol in at least 80% purity.

12. The process of claim 1, wherein the purified solution comprises the pinitol in at least 85% purity.

13. The process of claim 1, wherein the purified solution comprises the pinitol in at least 90% purity.

14. The process of claim 1, wherein the purified solution comprises the pinitol in at least 95% purity.

15. The process of claim 1, wherein the demineralized carob extract, prior to the chromatographically separating (2), has a pH in a range of from 2 to 4.5.

16. The process of claim 1, wherein the demineralized carob extract, prior to the chromatographically separating (2), has a pH in a range of from 2.5 to 3.5.

17. The process of claim 1, wherein the demineralized carob extract further comprises fructose in a range of from 20 to 50 wt. % and glucose in a range of from 20 to 50 wt. %, based on total demineralized carob extract weight.

18. The process of claim 1, wherein the demineralized carob extract further comprises fructose in a range of from 30 to 40 wt. % and glucose in a range of from 30 to 40 wt. %, based on total demineralized carob extract weight.

19. The process of claim 1, wherein the pinitol content of the aqueous solution obtained after the chromatographically separating (2) and before the purifying (g), is in a range of from 50 to 70 wt. %.

20. The process of claim 1, wherein the aqueous solution obtained after the chromatographically separating (2) and before the purifying (3), comprises pinitol in a range of from 60 to 70 wt. %, sucrose in a range of from 2 to 8 wt. %, glucose in a range of from 20 to 32 wt. %, and fructose in a range of from 0 to 6 wt. %.

* * * * *